United States Patent [19]

Heeres et al.

[11] 4,456,605

[45] Jun. 26, 1984

[54] HETEROCYCLIC DERIVATIVES OF [4-(PIPERAZIN-1-YL-PHENYLOXYMETHYL)-1,3-DIOXOLAN-2-YLMETHYL]-1H-IMIDAZOLES AND 1H-1,2,4-TRIAZOLES

[75] Inventors: Jan Heeres, Vosselaar; Robert Hendrickx, Beerse, both of Belgium

[73] Assignee: Janssen Pharmaceutica N.V., Beerse, Belgium

[21] Appl. No.: 509,562

[22] Filed: Jun. 30, 1983

Related U.S. Application Data

[60] Division of Ser. No. 261,420, May 7, 1981, Pat. No. 4,402,957, which is a division of Ser. No. 27,178, Apr. 4, 1979, Pat. No. 4,287,195, which is a continuation-in-part of Ser. No. 924,765, Jul. 14, 1978, abandoned.

[51] Int. Cl.$^3$ .................. C07D 419/14; A61K 31/52
[52] U.S. Cl. .................. 424/250; 424/251; 424/253; 544/333; 544/366; 544/369; 544/367; 544/359; 544/353; 544/354
[58] Field of Search .................. 424/250, 251, 253; 544/333, 353, 354, 366, 367, 369, 359

[56] References Cited

U.S. PATENT DOCUMENTS

| | | | |
|---|---|---|---|
| 4,160,841 | 7/1979 | Heeres et al. | 424/273 R |
| 4,287,195 | 9/1981 | Heeres et al. | 424/250 |
| 4,402,957 | 9/1983 | Heeres et al. | 424/250 |

*Primary Examiner*—Nicholas S. Rizzo
*Attorney, Agent, or Firm*—Geoffrey G. Dellenbaugh

[57] ABSTRACT

Novel heterocyclic derivatives of [4-(piperazin-1-yl-phenoxymethyl)-1,3-dioxolan-2-ylmethyl]-1H-imidazoles and 1H-1,2,4-triazoles, useful as antifungal and antibacterial agents.

2 Claims, No Drawings

HETEROCYCLIC DERIVATIVES OF [4-(PIPERAZIN-1-YL-PHENYLOXYMETHYL)-1,3-DIOXOLAN-2-YLMETHYL]-1H-IMIDAZOLES AND 1H-1,2,4-TRIAZOLES

CROSS-REFERENCE TO RELATED APPLICATIONS

This is a division of application Ser. No. 261,420, filed May 7, 1981, now U.S. Pat. No. 4,402,957, which in turn is a division of application Ser. No. 027,178, filed Apr. 4, 1979, now U.S. Pat. No. 4,287,195, which in turn is a continuation-in-part of application Ser. No. 924,765, filed July 14, 1978, now abandoned.

BACKGROUND OF THE INVENTION

In U.S. Pat. No. 3,936,470 and Belg. Pat. No. 837,831 there are described a number of 1-(1,3-dioxolan-2-ylmethyl)-1H-imidazoles and 1H-1,2,4-triazoles having antifungal and antibacterial properties. The compounds of this invention differ from the foregoing essentially by the substitution of the aryloxy-moiety with a piperazinyl group, substituted in the 4-position with a mono- or binuclear heteroaromatic radical. Similar compounds wherein a heterocyclic radical is attached directly to the aryloxy group are described in U.S. patent application Ser. No. 853,726, filed Nov. 21, 1977.

DESCRIPTION OF THE PREFERRED EMBODIMENTS

This invention is concerned with novel 1H-imidazole and 1H-1,2,4-triazole derivatives which may structurally be represented by the formula:

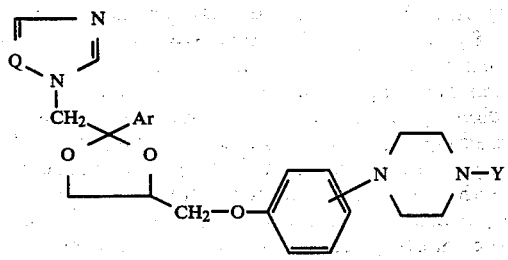

and the pharmaceutically acceptable acid addition salts and stereochemically isomeric forms thereof, wherein:

Q is a member selected from the group consisting of CH and N;

Ar is a member selected from the group consisting of phenyl, thienyl, halothienyl and substituted phenyl, said substituted phenyl having from 1 to 3 substituents each independently selected from the group consisting of halo, lower alkyl, lower alkyloxy and trifluoromethyl; and the radical Y is an optionally substituted mono- or binuclear nitrogen-containing heteroaromatic radical selected from the group consisting of:
a radical of formula

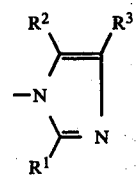

wherein $R^1$ is selected from the group consisting of hydrogen, lower alkylthio, aryllower alkylthio and arylthio and $R^2$ and $R^3$ are each independently selected from the group consisting of hydrogen, lower alkyl, aryl and aryllower alkyl;

a radical of formula

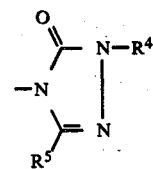

wherein each of $R^4$ and $R^5$ are independently selected from the group consisting of hydrogen, lower alkyl, aryl and aryllower alkyl;

a radical of formula

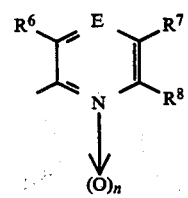

wherein n is the integer 0 or 1, E is a member selected from the group consisting of N and C—$R^9$ and $R^6$, $R^7$, $R^8$ and $R^9$ are each independently selected from the group consisting of hydrogen, halo, lower alkyl, lower alkyloxy, lower alkylthio, hydroxy, mercapto, nitro, amino and aminocarbonyl, or, $R^7$ and $R^8$, when taken together, represent a radical of the formula —CH=CH—CH=CH—;

a radical of formula

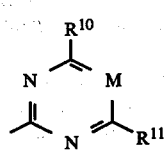

wherein M is a member selected from the group consisting of N and C—$R^{12}$ and $R^{10}$, $R^{11}$ and said $R^{12}$ are each independently selected from the group consisting of hydrogen, halo, lower alkyl, nitro and amino;

a radical of formula

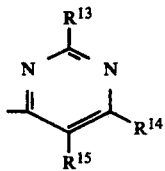
(e)

wherein $R^{14}$ and $R^{15}$ are each independently selected from the group consisting of hydrogen, halo, lower alkyl, lower alkyloxy, aryl and aryllower alkyl and $R^{13}$ is selected from the group consisting of hydrogen, halo, amino, lower alkylthio, aryllower alkylthio and lower alkyloxy;
a radical of formula

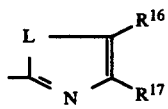
(f)

wherein L is a member selected from the group consisting of S and N—$R^{18}$, said $R^{18}$ being selected from the group consisting of hydrogen, lower alkyl and aryllower alkyl, and $R^{16}$ and $R^{17}$ are each independently selected from the group consisting of hydrogen, lower alkyl, nitro and aryllower alkyl, or $R^{16}$ and $R^{17}$, when taken together, represent a radical of the formula —CH=CH—CH=CH—; and
a radical of formula

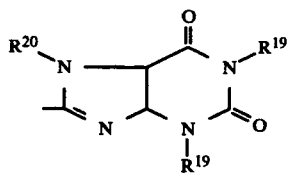
(g)

wherein $R^{19}$ and $R^{20}$ are each independently selected from the group consisting of hydrogen, lower alkyl and aryllower alkyl;
wherein said aryl as used in the foregoing definitions is selected from the group consisting of phenyl and substituted phenyl, said substituted phenyl having from 1 to 3 substituents each independently selected from the group consisting of halo, lower alkyl, lower alkyloxy and trifluoromethyl.

The preferred compounds of this invention are those wherein the 1-piperazinyl group is attached to the phenoxymethyl moiety in the 4-position of said phenyl group.

As used in the foregoing and in following definitions the term "halo" is generic to fluoro, chloro, bromo and iodo; and "lower alkyl" is meant to include straight and branched hydrocarbon radicals having from 1 to 6 carbon atoms such as, for example, methyl, ethyl, 1-methylethyl, 1,1-dimethylethyl, propyl, 1-methylpropyl, 2-methylpropyl, butyl, pentyl, hexyl and the like.

In order to simplify the structural representation of the compounds (I) and of certain starting materials and intermediates used in the preparation thereof, the 2-Ar-2-(1H-imidazol-1-ylmethyl or 1H-1,2,4-triazol-1-ylmethyl)-1,3-dioxolan-4-yl group, wherein Ar is as previously defined, will hereafter be represented by the symbol D:

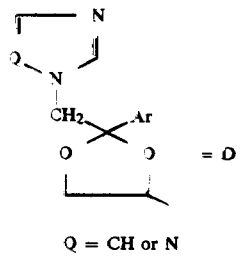

Q = CH or N

The compounds of formula (I) can generally be prepared by the reaction of an appropriate reactive ester of formula (II) with an appropriately substituted phenol of formula (III) by the application of standard O-alkylation procedures.

D—CH$_2$—W +

(II)

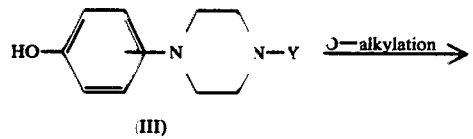

(III)

In formula (II), W has the meaning of a reactive ester residue such as, for example, halo, methylsulfonyloxy, 4-methylphenylsulfonyloxy and the like. The reaction of (II) with (III) is carried out under art-known conditions of performing O-alkylations with reactive esters. The reaction is generally carried out in an appropriate reaction-inert organic solvent such as, for example, N,N-dimethylformamide, N,N-dimethylacetamide, hexamethylphosphoric triamide, dimethylsulfoxide, 4-methyl-2-pentanone and the like, optionally in admixture with other reaction inert solvents such as, for example, aromatic hydrocarbons, e.g., benzene, methylbenzene, dimethylbenzene and the like. Further it is advantageous to add to the reaction mixture an appropriate base such as, for example, an alkali metal hydride or carbonate, in order to enhance the rate of the reaction. Otherwise it may be advantageous to first convert the substituted phenol (III) into a metal salt thereof, preferably the sodium salt, in the usual manner, e.g., by the reaction of (III) with metal bases such as sodium hydride, sodium hydroxide and the like, and to use thereafter said metal salt in the reaction with (II). Somewhat elevated temperatures are appropriate to enhance the reaction rate and most preferably the reaction is carried out at from about 80° C. to about 130° C.

The compounds of formula (I), wherein Y is as previously defined but other than a radical (a) or (b), said Y being represented by Ya and said compounds by the formula (I-a), can alternatively be prepared by N-alkylating an appropriately substituted piperazine of formula (IV) with an appropriate reactive ester of the formula (V), wherein W has the previously defined meaning, following standard N-alkylation procedures.

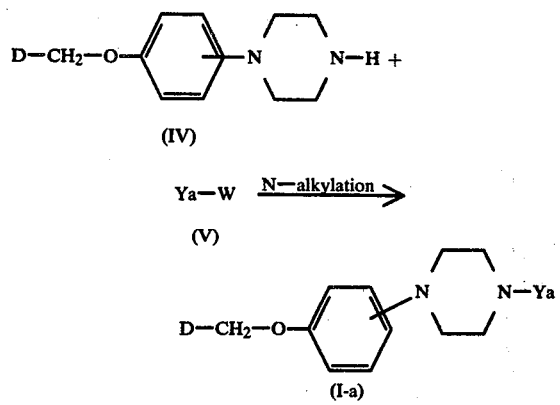

The reaction of (IV) with (V) is preferably conducted in a suitable reaction-inert organic solvent such as, for example, an alcohol, e.g., butanol and the like; an amide, e.g., N,N-dimethylformamide, N,N-dimethylacetamide, hexamethylphosphoric triamide and the like; dimethylsulfoxide; 4-methyl-2-pentanone and the like, optionally in admixture with a second reaction-inert organic solvent such as, for example, aromatic hydrocarbons, e.g., benzene, methylbenzene, dimethylbenzene and the like. Further it is advantageous to add to the reaction mixture an appropriate base such as, for example, an alkali metal hydride or carbonate, in order to enhance the reaction rate. Somewhat elevated temperatures are appropriate and most preferably the reaction is carried out at from about 80° C. to about 130° C.

The compounds of formula (I), wherein Y represents a radical of formula (a) wherein $R^1$ is other than hydrogen, said compounds being represented by the formula (I-b-1), can also be prepared by (i) stirring and heating an appropriate isothiocyanate (VI), wherein $R^{21}$ is lower alkyl or aryllower alkyl, with an appropriately substituted piperazinamine (VII) in the presence of a suitable reaction-inert organic solvent such for example, a halogenated hydrocarbon, e.g., dichloromethane;

(ii) subsequently converting the thus obtained thiourea (VIII) to the corresponding carbamimidothioate (X) with an halogenide (IX), wherein $R^{1'}$ is lower alkyl, aryl or aryllower alkyl and halo is preferably chloro, bromo or iodo, by stirring the reactants together in the presence of an appropriate reaction-inert organic solvent, e.g., ethyl acetate, and, most preferably, in the presence of an organic acid, e.g., acetic acid, in order to prevent quaternization of the tertiary amino groups, and (iii) cyclizing the thus obtained carbamimidothioate (X) by stirring and heating the latter in an aqueous acidic medium, e.g., in aqueous hydrochloric acid.

The foregoing reactions are schematically represented as follows:

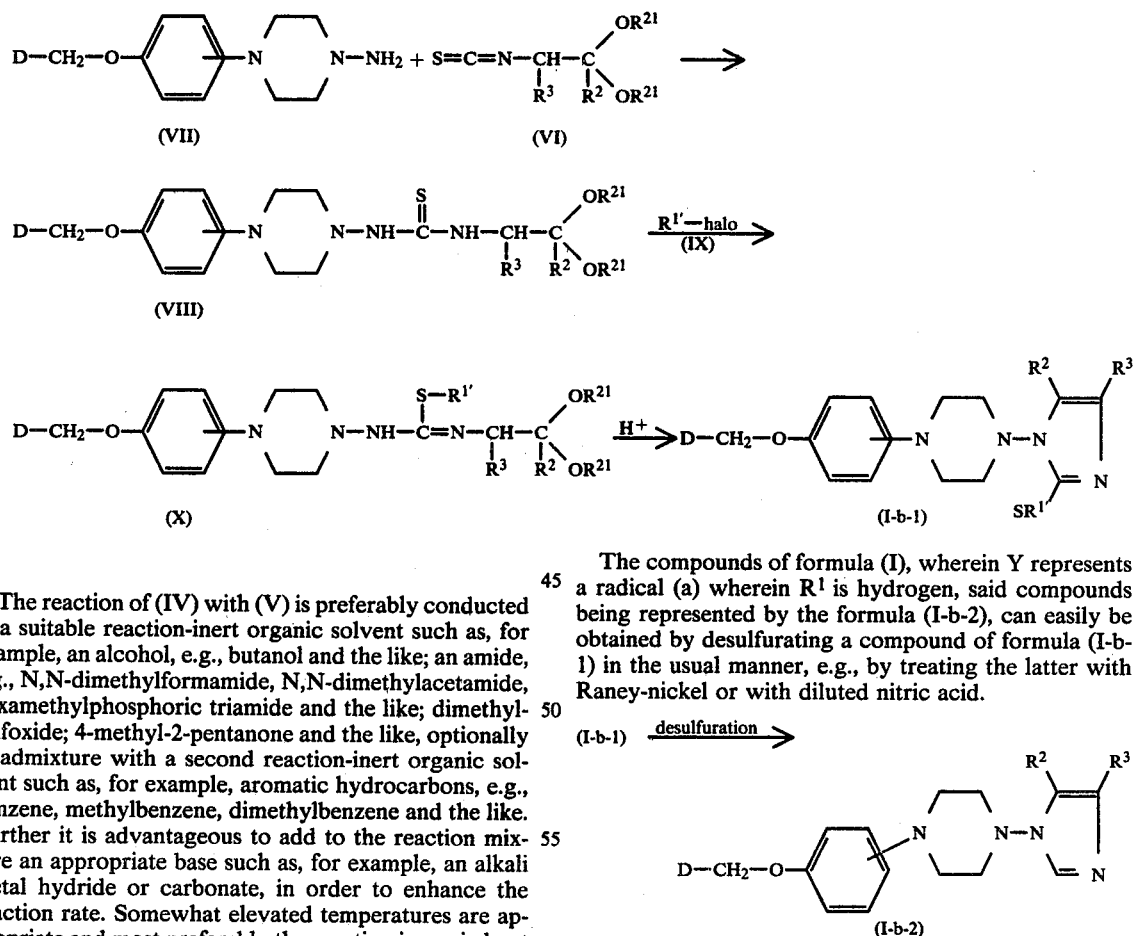

The compounds of formula (I), wherein Y represents a radical (a) wherein $R^1$ is hydrogen, said compounds being represented by the formula (I-b-2), can easily be obtained by desulfurating a compound of formula (I-b-1) in the usual manner, e.g., by treating the latter with Raney-nickel or with diluted nitric acid.

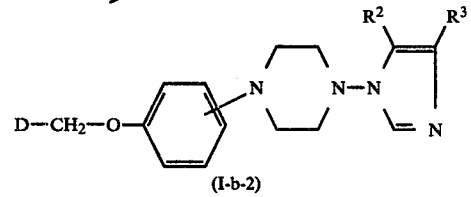

The compounds of formula (I), wherein Y represents a radical (b) wherein $R^4$ is hydrogen and $R^5$ is as previously defined, said compounds being represented by the formula (I-c-1), may be prepared by (i) stirring an appropriately substituted piperazinamine (VII) with an appropriate carbonochloridate (XI), wherein $R^{22}$ is lower alkyl, aryl or aryllower alkyl, in a suitable reaction-inert solvent, such as, for example, a halogenated hydrocarbon, e.g., trichloromethane and the like, preferably in the presence of a suitable base, such as pyridine, N,N-diethylethanamine and the like, in order to neutralize the hydrochloric acid, liberated during the coarse of the reaction;

(ii) subsequently reacting the thus obtained carbamate (XII) with hydrazine by stirring and heating the reactants together in the presence of a suitable reaction-inert solvent such as, for example, a cyclic ether, e.g., 1,4-dioxane, tetrahydrofuran and the like; and (iii) cyclizing the thus obtained hydrazinecarboxamide (XIII) with an appropriately substituted imidamide (XIV) by heating and melting the reactants as such or, if desired, in the presence of a suitable solvent, e.g., water, acetic acid and the like.

The foregoing reactions are schematically represented as follows:

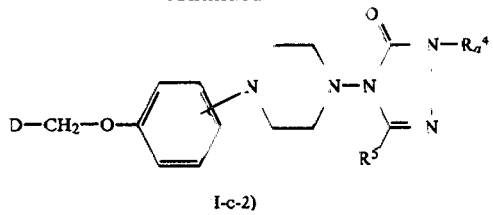

(I-c-2)

The compounds of formula (I), wherein Y represents a radical (f), wherein $R^{16}$ and $R^{17}$ are hydrogen, lower alkyl or aryllower alkyl and L is S, said compounds being represented by the formula (I-d), can be prepared by (i) stirring and heating an appropriately substituted

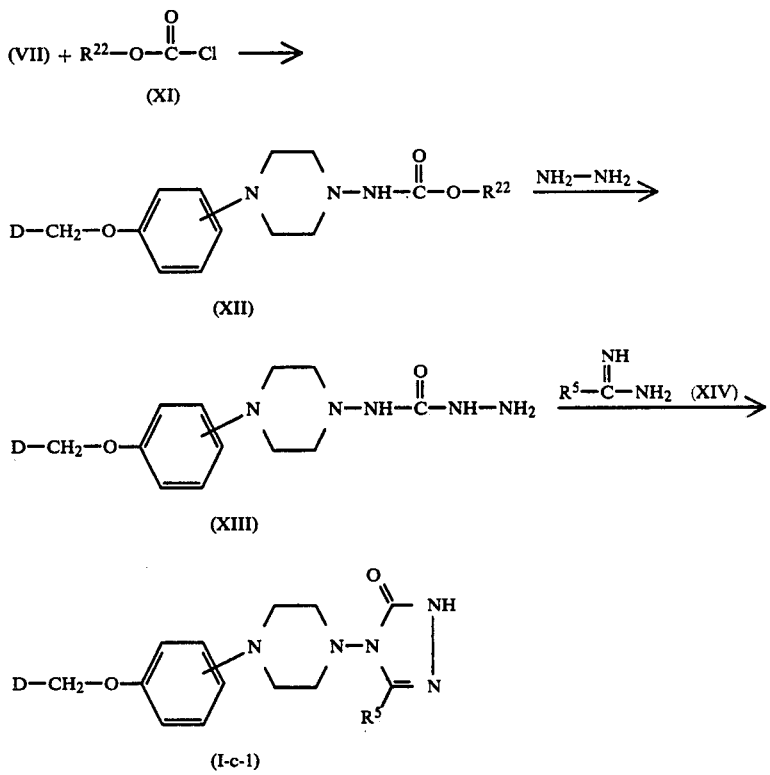

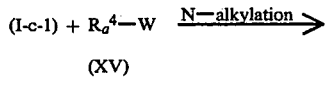

piperazine (IV) with an appropriate isothiocyanate (XVI) wherein $R^{16}$, $R^{17}$ and $R^{21}$ are as previously defined, in the presence of a suitable reaction-inert solvent such as, for example, an alkanol, e.g., methanol and the like, preferably in the presence of an appropriate base such as, for example, an alkali- or an earth alkaline metal hydroxide, e.g., sodium hydroxide and the like;

(ii) subsequently cyclizing the thus obtained carbothioamide (XVII) in aqueous acidic medium, e.g., aqueous hydrochloric acid and the like; and (iii) eliminating the $R^{21}O$-group of the thus obtained 4,5-dihydrothiazole (XVIII) using a strong non-oxidizing acid such as, for example hydrobromic acid in glacial acetic acid.

The foregoing reactions are schematically represented as follows

The compounds of formula (I) wherein Y represents a radical (b), wherein $R^4$ is lower alkyl, aryl or aryllower alkyl said $R^4$ being represented by $R^4_a$ and wherein $R^5$ is as previously defined, said compounds being represented by the formula (I-c-2), may be derived from a compound of formula (I-c-1) by N-substituting the latter with a reactant by formula (XV), wherein $R^4$ and W are as previously defined, following standard N-alkylating procedures as described hereabove.

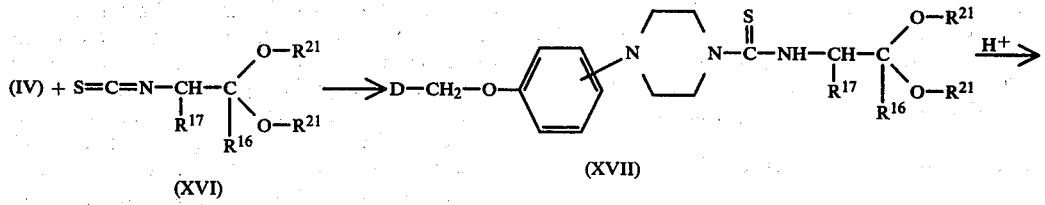

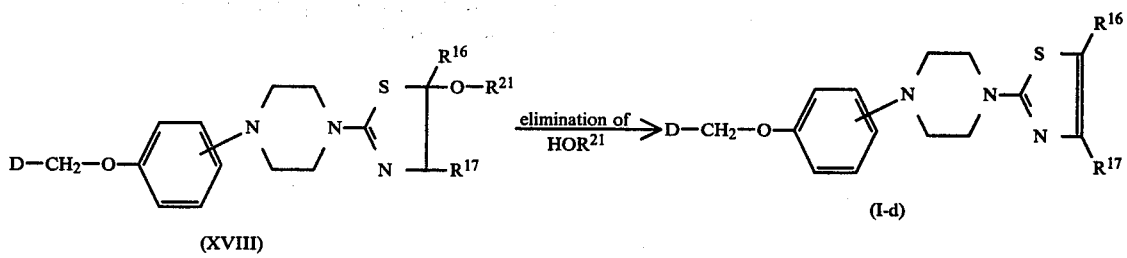

The imidazole derivatives of formula (I), obtained in base form in the foregoing preparations, may be converted to their therapeutically useful acid addition salts by reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; an organic acid such as acetic, propanoic, hydroxyacetic, 2-hydroxypropanoic, 2-oxopropanoic, ethanedioic, propanedioic, 1,4-butanedioic, (Z)-2-butenedioic, (E)-2-butenedioic, 2-hydroxy-1,4-butanedioic, 2,3-dihydroxy-1,4-butanedioic, 2-hydroxy-1,2,3-propanetricarboxylic, benzoic, 3-phenyl-2-propenoic, α-hydroxybenzeneacetic, methanesulfonic, ethanesulfonic, 2-hydroxyethanesulfonic, 4-methylbenzenesulfonic, 2-hydroxybenzoic, 4-amino-2-hydroxybenzoic, 2-phenoxybenzoic or 2-acetyloxybenzoic acid. The salts are in turn converted to the corresponding free bases in the usual manner, e.g., by reaction with alkali such as sodium or potassium hydroxide.

A number of the intermediates and starting materials used in the foregoing preparations are known compounds, others may be prepared according to art-known methodologies of preparing similar compounds and some of them are novel and consequently their preparation will be described hereafter.

The intermediates of formula (III) wherein Y is as previously described but other than a radical (a) or (b), said Y being represented by Ya and said intermediates by the formula (III-a), can be prepared by N-alkylating an appropriately substituted piperazine (XIX), wherein $R^{22}$ is hydrogen or lower alkyl, with an appropriate reactive ester (V), wherein W is a previously defined, following the same procedure as previously described hereabove for the preparation of (I-a) starting from (IV) and (V), and, in case $R^{22}$ is lower alkyl, subsequently converting the lower alkyloxy group of the thus obtained (XX) into a hydroxy group, e.g., by acid hydrolysis using a strong non-oxidizing acid, such as, hydrobromic acid in glacial acetic acid and the like.

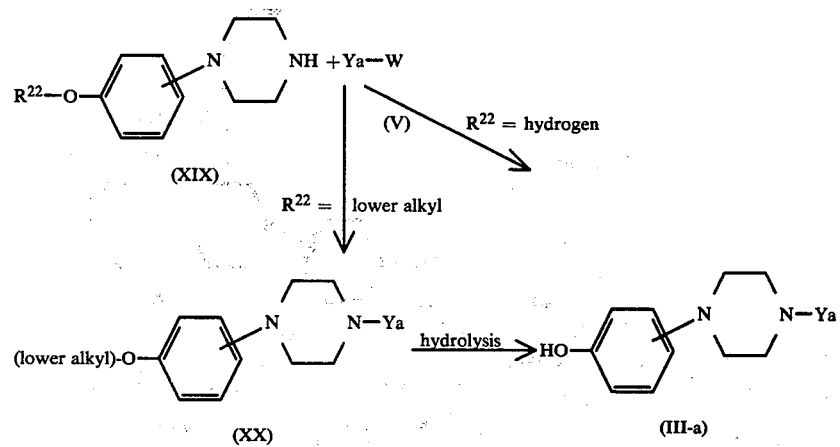

The intermediates of formula (III) wherein Y represents a radical (a), said intermediates being represented by the formula (III-b), can be derived from an appropriately substituted piperazinamine (XXI), wherein $R^{22}$ is as previously defined, following one of the procedures previously described herein for the preparation of (I-b-1) and (I-b-2) starting from (VII) and (VI), and, in case $R^{22}$ is lower alkyl, subsequently converting the lower alkyloxy group of the thus obtained (XXII) into a hydroxyl group such as, for example, by hydrolysis, e.g., by using hydrobromic acid in glacial acetic acid.

The intermediates of formula (III), wherein Y represents a radical (b), said intermediates being represented by the formula (III-c), can be prepared starting from an appropriately substituted piperazinamine (XXI) following one of the procedures previously described herein for the preparations of (I-c-1) and (I-c-2) starting from (VII) and (XI), and, in case $R^{22}$ is lower alkyl, subsequently converting the lower alkyloxy group of the thus obtained (XXIII) into a hydroxyl group, e.g., by acid hydrolysis with hydrobromic acid in glacial acetic acid.

The foregoing reactions are schematically represented as follows:

The intermediates of formula (III), wherein Y represents a radical (f) wherein $R^{16}$ and $R^{17}$ are hydrogen, lower alkyl or aryllower alkyl and L is S, said intermediates being represented by the formula (III-d), can be derived from an appropriate piperazine (XIX), wherein $R^{22}$ is as previously defined, following the same procedure as described hereabove for the preparation of (I-d) starting from (IV) and, in case $R^{22}$ is lower alkyl, subsequently hydrolyzing the lower alkyloxy group of the thus obtained (XXIV), e.g., by using hydrobromic acid in glacial acetic acid.

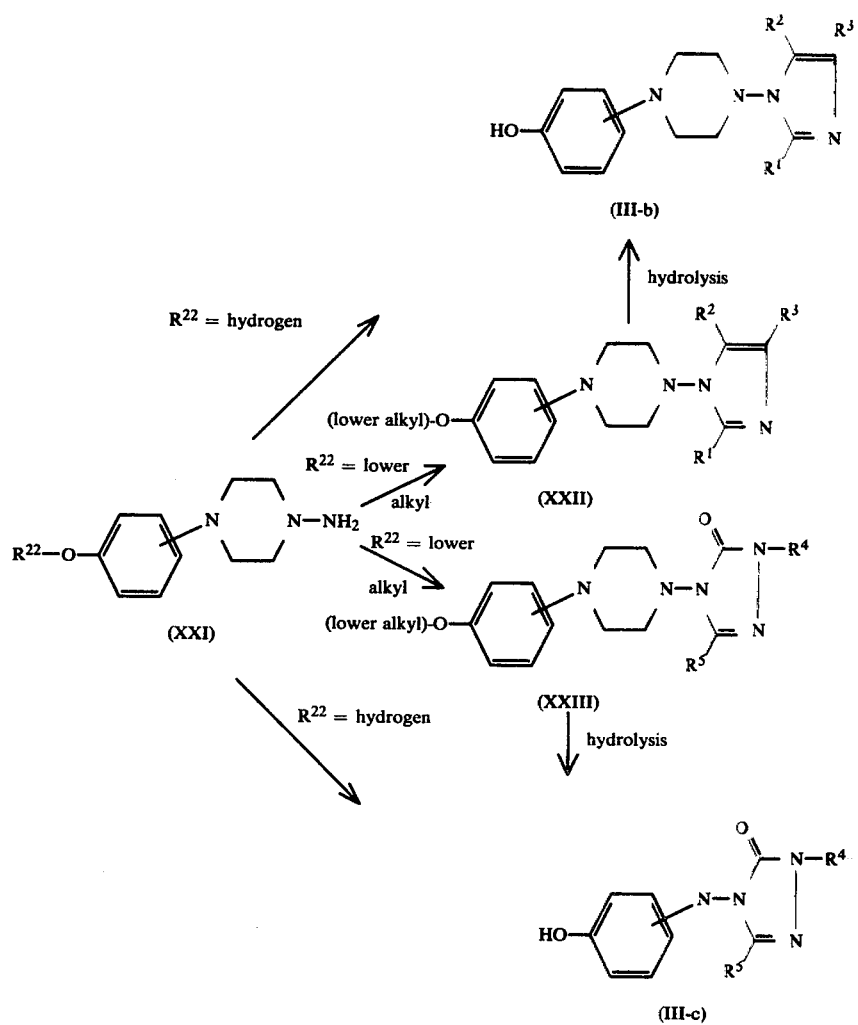

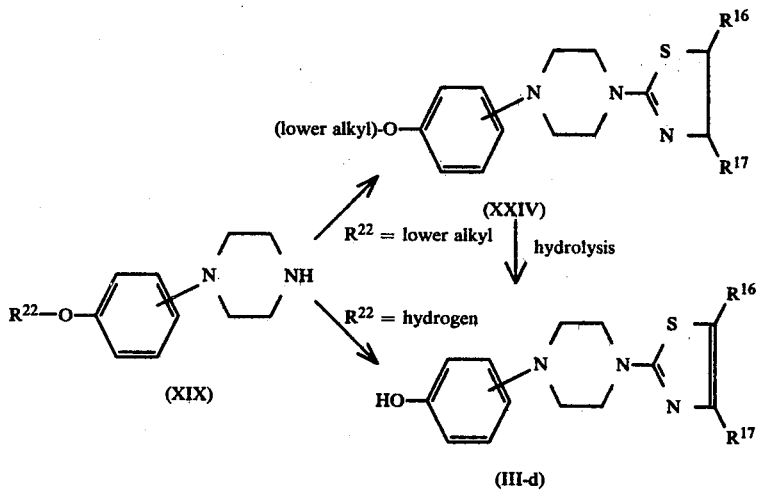

The intermediates of formula (IV) can be prepared by O-alkylating an appropriately substituted phenol (XXV), wherein P represents a suitable protecting group such as, for example, a phenylmethyl radical, a 2-methylethenyl radical and the like, with an appropriate reactive ester of formula (II), following standard O-alkylation procedures as previously described herein for the preparation of (I) starting from (II) and (III), and subsequently eliminating the protective group of the thus obtained (XXVI) by classical means, depending upon the nature of P, e.g., by catalytically hydrogenating the phenylmethyl derivatives or by hydrolyzing the 2-methylethenyl derivatives in acidic aqueous medium.

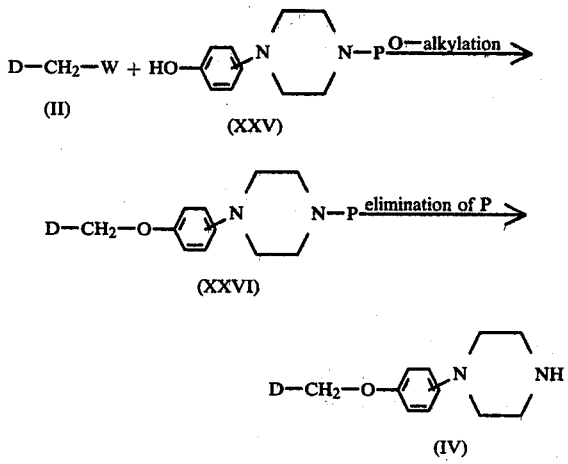

Following the same procedure as described for the preparation of (IV) starting from (II) and by using an appropriate reactive ester of the formula (XXVII) instead of the reactive ester (II) used therein, the corresponding starting materials of formula (XIX) are conveniently obtained.

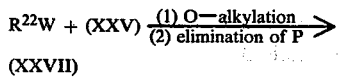

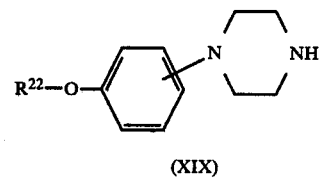

The intermediates of formula (VII) can easily be prepared by (i) reacting a piperazine (IV) with nitrous acid or a salt thereof such as, for example, sodium nitrite and the like, in acidic medium, e.g., acetic acid, in the presence of an appropriate relatively polar solvent such as, for example, water, if desired, in admixture with a water-miscible solvent, e.g., 1,4-dioxane, and most preferably at a reduced temperature; and (ii) subsequently reducing the thus obtained nitrosopiperazine (XXVIII) with an appropriate reducing agent, such as, for example, an appropriate complex metal hydride, e.g., lithium aluminium hydride, in the presence of a suitable reaction-inert organic solvent such as, for example, tetrahydrofuran, preferably in admixture with a second reaction-inert organic solvent such as, for example, an aromatic hydrocarbon, e.g., benzene and the like.

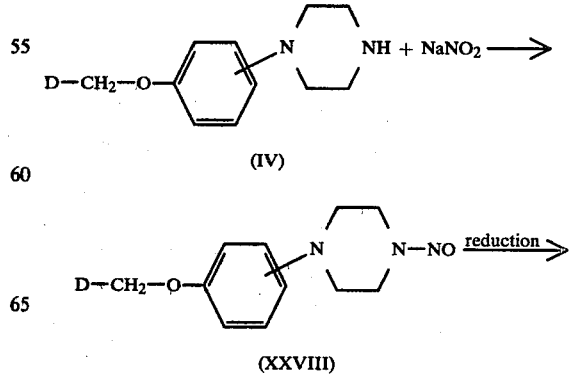

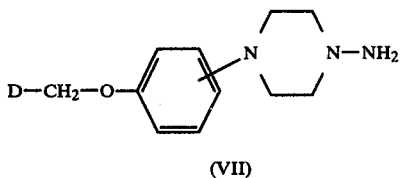

(VII)

Starting from (XIX) the starting materials of formula (XXI) may be prepared following the same procedure as described hereabove for the preparation of (VII) starting from (IV).

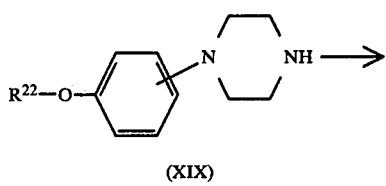

(XIX)

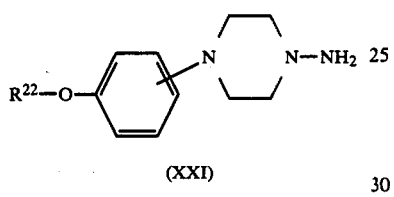

(XXI)

Starting materials of formula (II) wherein Q is CH and methods of preparing the same are described in U.S. Pat. No. 4,144,346. In general the reactive esters of formula (II) can be prepared along the following sequence of reactions.

An appropriate 1-Ar-2-bromoethanone of formula (XXIX) is subjected to an acetalization reaction with 1,2,3-propanetriol following methodologies analogous to those described in Synthesis, 1974, (I), 23.

In a preferred manner of carrying out the reaction both reactants are refluxed together for several hours with azeotropic water removal in an appropriate organic solvent, preferably in the presence of a simple alcohol, such as, for example, ethanol, propanol, butanol, pentanol and the like, and in the presence of an appropriate strong acid such as 4-methylbenzenesulfonic acid. Suitable organic solvents are, for example, aromatic hydrocarbons, such as benzene, methylbenzene, dimethylbenzene and the like and saturated hydrocarbons, such as cyclohexane.

The thus obtained dioxolane (XXX) is then reacted with benzoyl chloride to obtain a benzoate of the formula (XXXI) and the latter is subsequently reacted with 1H-imidazole or 1H-1,2,4-triazole. Said reaction is preferably carried out by stirring and heating the reactants together in a suitable organic solvent, e.g., N,N-dimethylformamide, in the presence of an appropriate strong metal base, e.g., sodium methanolate, to obtain an intermediate of the formula (XXXII). The desired reactive esters of formula (II) are then conveniently prepared by first hydrolyzing (XXXII) in alkaline medium and thereafter converting the hydroxy group of the thus obtained (XXXIII) into a reactive ester thereof according to methodologies generally known in the art. For example, methanesulfonates and 4-methylbenzenesulfonates are conveniently prepared by the reaction of the alcohol with methanesulfonyl chloride or 4-methylbenzenesulfonyl chloride and halides may be prepared by the reaction of the alcohol with an appropriate halogenating agent such as, for example, thionyl chloride, sulfuryl chloride, phosphor pentachloride, phosphor pentabromide, phosphoryl chloride and the like. When the reactive ester is an iodide, it is preferably derived from the corresponding chloride or bromide by the replacement of that halogen with iodine.

The foregoing reactions may be illustrated as follows:

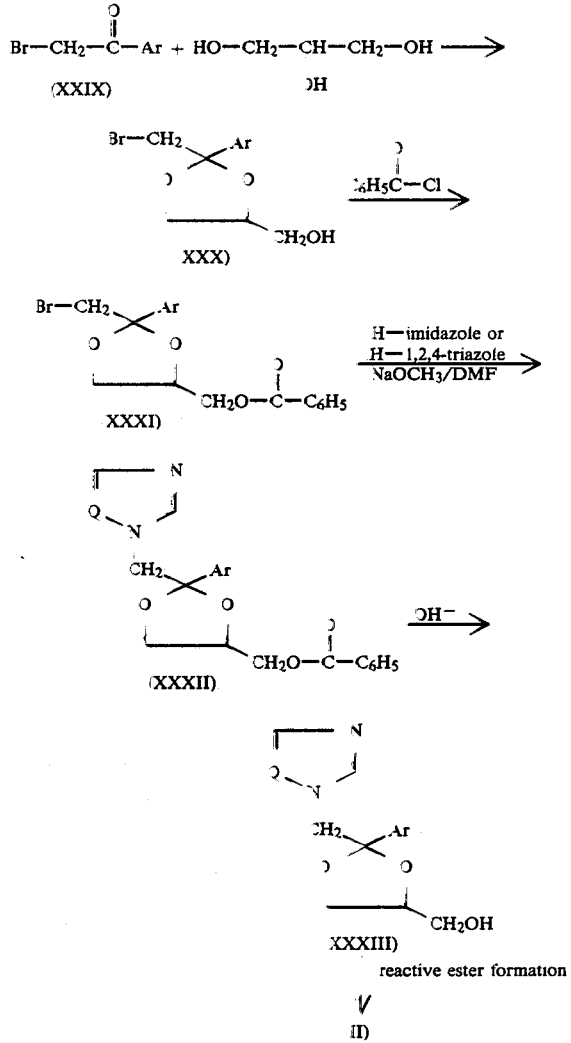

From formula (I) it is evident that the compounds of this invention have at least two asymmetric carbon atoms in their structures, namely those located in the 2- and 4-position of the dioxolane nucleus, and consequently they can exist under different stereochemically isometric forms. The stereochemically isomeric forms of (I) and the pharmaceutically acceptable acid addition salts thereof are intended to be within the scope of this invention.

The diastereomeric racemates of (I), denoted as cis and trans forms respectively, according to the rules described in C.A., 76, Index Guide, Section IV, p. 85 (1972), may be obtained separately by conventional methods. Appropriate methods which may advantageously be employed therefore include, for example, selective crystallization and chromatographic separation, e.g., column-chromatography.

Since the stereochemical configuration is already fixed in the intermediates (II) and (IV) it is also possible to separate cis and trans forms at this or even at earlier stage, whereupon the corresponding forms of (I) may be derived therefrom in the previously indicated manner. The separation of cis and trans forms of such intermediates may be performed by conventional methods as described hereabove for the separation of cis and trans forms of the compounds (I).

It is evident that the cis and trans diastereomeric racemates may be further resolved into their optical isomers, cis(+), cis(−), trans(+) and trans(−) by the application of methodologies known to those skilled in the art.

The compounds of formula (I) and the pharmaceutically acceptable acid addition salts thereof are useful agents in combatting fungi and bacteria. For example, said compounds and acid addition salts thereof were found to be highly active against a wide variety of fungi such as, for example, *Microsporum canis, Ctemomyces mentagrophytes, Trichlophyton rubrum, Phialophora verrucosa, Cryptococcus neoformans, Candida tropicalis, Candida albicans,* Mucor species, *Aspergillus fumigatus, Sporotricum schenckii* and Saprolegnia species, and against bacteria such as, for example, *Erysipelotrix insidiosa,* Straphylococci such as *Staphylococcus hemolyticus* and Streptococci such as *Streptococcus pyogenes.* In view of their potent, local as well as systemic, antimicrobial activity the compounds of this invention constitute useful tools for the destruction or prevention of the growth of fungi and bacteria and more particularly they can effectively be used in the treatment of subjects suffering from such microorganism.

The strong antimicrobial activity of the compounds (I) is clearly evidenced by the data obtained in the following experiments, which data is only given to illustrate the useful antimicrobial properties of all the compounds (I) and not to limit the invention either with respect to the scope of susceptible microorganisms nor with respect to the scope of formula (I).

Experiment A

Activity of compounds (I) against vaginal candidosis in rats

Female Wistar rats of ±100 g body weight are used. They are ovariectomized and hysterectomized and after three weeks of recovery, 100 μg of oestradiol undecylate in sesame oil is given subcutaneously once a week for 3 consecutive weeks. The thus induced pseudocestrus is controlled by microscopic examination of vaginal smears. Food and water are left available ad libitum. The rats are infected intravaginally with $8.10^5$ cells of *Candida albicans,* grown on Sabouraud broth for 48 hours at 37° C. and diluted with saline. The date of infection varies from day +25 to day +32 after surgical intervention, depending on the appearance of signs of induced pseudocestrus.

The drugs under investigation are administered orally once a day for two days starting from the day of infection. For each experiment there are placebo treated controls. The results are assessed by taking vaginal smears with sterile swabs on several days after the infection. The swabs are put into Sabouraud broth in petri-dishes and incubated for 48 hours at 37° C. If no growth of *Candida albicans* occurs, i.e., when the animals are negative at the end of the experiment, this is due to drug administration because it never happens in placebo treated controls.

The table below gives the lowest oral dose of the drug under investigation which is found active at the 14th day after infection.

Experiment B

Activity of compounds (I) against crop candidosis in turkeys

Turkeys of 14 days old are infected in the crop with $4.10^6$ *Candida albicans* cells, grown on Sabouraud broth for 48 hours at 37° C. and diluted with saline. The volume of the inoculum is 1 ml. The drugs under investigation are premixed in 500 mg of lacton and thereafter admixed in 1000 g of meal without any additives. The concentration of the drug under investigation in the meal is expressed in mg/kg.

The animals are given the medicated feed for 13 consecutive days starting on the day of infection. At the end of the experiment all animals are sacrificed. At autopsy the crops are removed, emptied and grinded in an ultra-turrax mixer in 15 ml of sterile saline. Colony counting is done on Sabouraud agar and the results given in the table represents the $ED_{50}$, i.e., the dose of the drug whereby the crops of 50% of the animals are completely negative for *Candida albicans.*

The compounds listed in the table are intended to illustrate and not to limit the scope of the present invention.

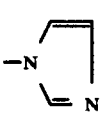
| Y | Q | Vaginal candidosis in rats: lowest effective dose in mg/kg orally | Crop candidosis in turkeys: ED$_{50}$ in mg/kg feed |
|---|---|---|---|
| 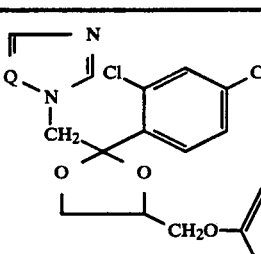 | —CH— | 1.25 | — |
| 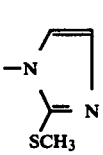 | —CH— | — | 8 |
| 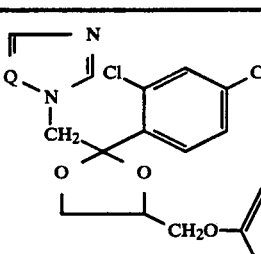 | —CH— | — | 16 |
| 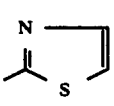 | —CH— | 2.5 | 31 |
| 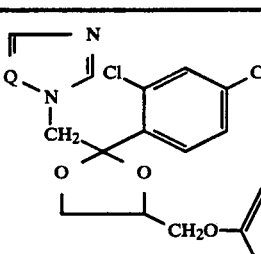 | —CH— | — | 16 |
| 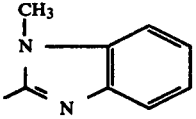 | —CH— | 2.5 | 16 |
| 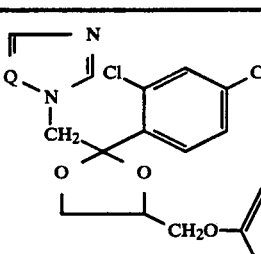 | N | 2.5 | 16 |
| 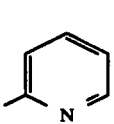 | N | <2.5 | <31 |
| 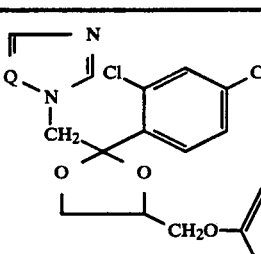 | N | 2.5 | — |

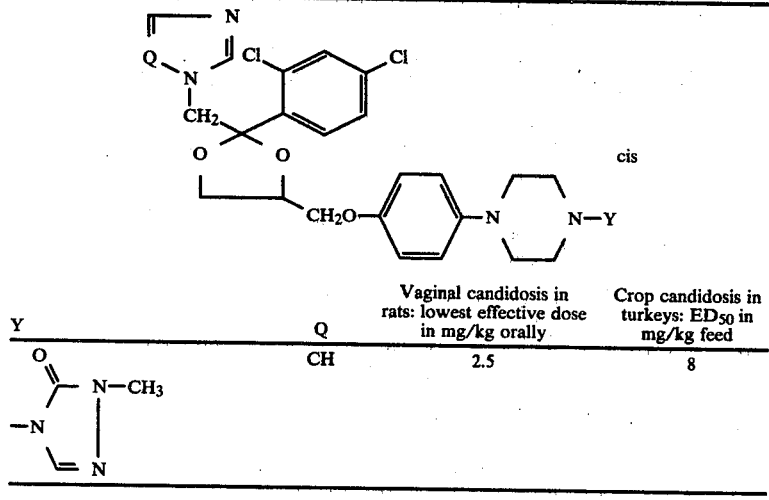

| Y | Q | Vaginal candidosis in rats: lowest effective dose in mg/kg orally | Crop candidosis in turkeys: ED$_{50}$ in mg/kg feed |
|---|---|---|---|
| (see structure) | CH | 2.5 | 8 |

In view of their antifungal and antibacterial properties this invention provides valuable compositions comprising the subject compounds of formula (I) or acid addition salts thereof as the active ingredient in a solvent or a solid, semi-solid or liquid diluent or carrier, and, in addition, it provides an effective method of combatting fungal or bacterial growth by use of an effective antifungal or antibacterial amount of such compounds (I) or salts thereof. Antifungal and antibacterial compositions comprising an effective amount of an active compound (I), either alone or in combination with other active therapeutic ingredients, in admixture with suitable carriers may be readily prepared according to conventional pharmaceutical techniques for the usual routes of administration.

Preferred compositions are in dosage unit form, comprising per dosage unit an effective quantity of the active ingredient in admixture with suitable carriers. Although the amount of the active ingredient per unit dosage may vary within rather wide limits, dosage units comprising from about 50 to about 500 mg and more particularly from about 100 to about 250 mg of the active ingredient are preferred.

The following examples are intended to illustrate and not to limit the scope of the present invention.

Unless otherwise stated all parts therein are by weight.

EXAMPLE I

To a stirred mixture of 52.6 parts of 1-(4-methoxyphenyl)piperazine dihydrochloride, 100 parts of acetic acid and 100 parts of water is added dropwise, during a 1.50 hours-period, a solution of 20.8 parts of sodium nitrite in 100 parts of water at a temperature between 0° and 5° C. Upon completion, stirring is continued for 30 minutes. The reaction mixture is diluted with water. The precipitated product is filtered off and crystallized from 2-propanol, yielding 22.5 parts of 1-(4-methoxyphenyl)-4-nitrosopiperazine; mp. 94.5° C.

To a stirred suspension of 10 parts of lithium aluminium hydride in 900 parts of tetrahydrofuran is added dropwise, during a 20 hours period, a solution of 40 parts of 1-(4-methoxyphenyl)-4-nitrosopiperazine in 720 parts of benzene. Upon completion, stirring is continued for 20 hours at room temperature. The reaction mixture is decomposed by the successive dropwise additions of 10 parts of water, 7.5 parts of a sodium hydroxide solution 50% and 30 parts of water. The whole is filtered and the filtrate is evaporated. The residue is purified by column-chromatography over silica gel using a mixture of trichloromethane and methanol (98:2 by volume) as eluent. The pure fractions are collected and the eluent is evaporated. The residue is crystallized from 1,1'-oxybisbutane. The product is filtered off and dried, yielding 18.56 parts of 4-(4-methoxyphenyl)-1-piperazinamine; mp. 107° C.

EXAMPLE II

A mixture of 8.3 parts of 4-(4-methoxyphenyl)-1-piperazinamine, 5.9 parts of 1-isocyanato-2,2-dimethoxyethane and 130 parts of dichloromethane is stirred and refluxed for 1 hour. The reaction mixture is evaporated and the residue is crystallized from 4-methyl-2-pentanone. The product is filtered off and dried, yielding 8.9 parts (63%) of N-(2,2-dimethoxyethyl)-N'-[4-(4-methoxyphenyl)-1-piperazinyl]thiourea; mp. 156.6° C.

A mixture of 17.3 parts of N-(2,2-dimethoxyethyl)-N'-[4-(4-methoxyphenyl)-1-piperazinyl]thiourea, 17 parts of iodoethane, 180 parts of ethyl acetate and 20 parts of acetic acid is stirred for 3 hours. Upon the addition of 2,2'-oxybispropane, the product is precipitated. It is filtered off and triturated in 4-methyl-2-pentanone. The product is filtered off and crystallized from 2-propanol, yielding 9 parts of ethyl N-(2,2-dimethoxyethyl)-N'-[4-(4-methoxyphenyl)-1-piperazinyl]carbamimidothioate monohydroiodide.

A mixture of 9 parts of ethyl N-(2,2-dimethoxyethyl)-N'-[4-(4-methoxyphenyl)-1-piperazinyl]carbamimidothioate monohydroiodide and 100 parts of a hydrochloric acid solution 6N is stirred and refluxed for 1 hour. The reaction mixture is cooled and adjusted to pH 10 with a sodium hydroxide solution 50%. The product is extracted with dichloromethane. The extract is dried, filtered and evaporated. The residue is crystallized from 1,1'-oxybisbutane (activated charcoal), yielding 6 parts (100%) of 1-[2-(ethylthio)-1H-imidazol-1-yl]-4-(4-methoxyphenyl)piperazine; mp. 111.8° C.

EXAMPLE III

A mixture of 5.3 parts of N-(2,2-dimethoxyethyl)-N'-[4-(4-methoxyphenyl)-1-piperazinyl]thiourea, 6 parts of iodomethane, 5 parts of acetic acid and 90 parts of ethyl acetate is stirred for 2 days at room temperature. Upon the addition of 2,2'-oxybispropane, the product is crystallized. It is filtered off and dried, yielding 6 parts (80%) of methyl N-(2,2-dimethoxyethyl)-N'-[4-(4-methoxyphenyl)-1-piperazinyl]carbamimidothioate monohydroiodide.

A mixture of 6 parts of methyl N-(2,2-dimethoxyethyl)-N'-[4-(4-methoxyphenyl)-1-piperazinyl]carbamimidothioate monohydroiodide and 30 parts of a hydrochloric acid solution 6N is stirred and refluxed for 1 hour. The reaction mixture is cooled and adjusted to pH 10 with sodium hydroxide a solution. The precipitated product is filtered off and crystallized from 4-methyl-2-pentanone, yielding 3.7 parts (100%) of 1-(4-methoxyphenyl)-4-[2-(methylthio)-1H-imidazol-1-yl]piperazine, mp. 140.1° C.

EXAMPLE IV

A mixture of 5.5 parts of 1-(4-methoxyphenyl)-4-[2-(methylthio)-1H-imidazol-1-yl]piperazine, 8 parts of Raney-nickel catalyst and 80 parts of methanol is stirred and refluxed overnight. The Raney-nickel is filtered off and another 8 parts of Raney-nickel catalyst are added. The whole is further stirred and refluxed overnight. The reaction mixture is filtered and the filtrate is evaporated. The residue is crystallized from 1,1'-oxybisbutane. The product is filtered off and dried, yielding 3.6 parts (77%) of 1-(1H-imidazol-1-yl)-4-(4-methoxyphenyl)piperazine, mp. 158.6° C.

EXAMPLE V

A mixture of 10.8 parts of 4-(1-piperazinyl)phenol dihydrobromide, 2.6 parts of 2-isothiocyanato-1,1-dimethoxyethane and 54 parts of methanol is stirred and refluxed for 30 minutes. Then there are added 4.7 parts of sodium hydroxide and the whole is stirred overnight at room temperature. The precipitated product is filtered off and crystallized from 4-methyl-2-pentanone, yielding 4.9 parts of N-(2,2-dimethoxyethyl)-4-(4-hydroxyphenyl)-1-piperazinecarbothioamide; mp. 161.4° C.

A mixture of 6 parts of N-(2,2-dimethoxyethyl)-4-(4-hydroxyphenyl)-1-piperazinecarbothioamide and 25 parts of a diluted hydrochloric acid solution is stirred overnight at room temperature. Upon the addition of sodium hydrogen carbonate, the product is allowed to crystallize. It is filtered off and recrystallized from ethanol, yielding 4.3 parts (73%) of 4-[4-(4,5-dihydro-5-methoxy-2-thiazolyl)-1-piperazinyl]phenol; mp. 165.6° C.

A mixture of 4 parts of 4-[4-(4,5-dihydro-5-methoxy-2-thiazolyl)-1-piperazinyl]phenol and 150 parts of a hydrobromic acid solution 48% is stirred and refluxed for 12 hours. The reaction mixture is evaporated and the residue is dissolved in water. The precipitated product is filtered off and crystallized from 4-methyl-2-pentanone. The product is filtered off and dried, yielding 2.5 parts (68%) of 4-[4-(2-thiazolyl)-1-piperazinyl]phenol; mp. 169.9° C.

EXAMPLE VI

A mixture of 10.6 parts of 1-(4-methoxyphenyl)piperazine dihydrobromide, 7.9 parts of 2-bromopyridine, 8.4 parts of potassium carbonate and 90 parts of N,N-dimethylformamide is stirred and refluxed overnight. The reaction mixture is diluted with water and the product is extracted twice with benzene. The combined extracts are dried, filtered and evaporated. The residue is crystallized from 1,1'-oxybisbutane. The product is filtered off and dried, yielding 8 parts (74%) of 1-(4-methoxyphenyl)-4-(2-pyridinyl)piperazine; mp. 125.6° C.

EXAMPLE VII

A mixture of 10.2 parts of 4-(1-piperazinyl)phenol dihydrobromide, 5.7 parts of 2-chloroquinoline, 6.3 parts of potassium carbonate and 80 parts of 1-butanol is stirred and refluxed overnight. The reaction mixture is diluted with water and 2,2'-oxybispropane is added: the product is crystallized. It is filtered off and recrystallized from 4-methyl-2-pentanone, yielding 6.4 parts (70%) of 4-[4-(2-quinolinyl)-1-piperazinyl]phenol; mp. 198.1° C.

EXAMPLE VIII

To a stirred solution of 8 parts of 4-(4-methoxyphenyl)-1-piperazinamine in 5 parts of pyridine and 45 parts of trichloromethane are added dropwise during a 30 minutes period 7.8 parts of phenyl carbonochloridate. Upon completion, stirring is continued for 30 minutes at room temperature. Water is added to the reaction mixture and the product is extracted with trichloromethane. The extract is dried, filtered and evaporated. The residue is triturated in 4-methyl-2-pentanone. The product is filtered off and crystallized from 1,4-dioxane, yielding 9 parts (70%) of phenyl [4-(4-methoxyphenyl)-1-piperazinyl]carbamate.

A mixture of 8 parts of phenyl [4-(4-methoxyphenyl)-1-piperazinyl]carbamate, 15 parts of hydrazine and 50 parts of 1,4-dioxane is stirred and refluxed for 4 hours. The reaction mixture is evaporated. The residue is triturated in 2-propanol. The product is filtered off and crystallized from 1-butanol, yielding 6.5 parts (84%) of N-[4-(4-methoxyphenyl)-1-piperazinyl]hydrazinecarboxamide.

EXAMPLE IX 6.5 Parts of N-[4-(4-methoxyphenyl)-1-piperazinyl]hydrazinecarboxamide and 6.5 parts of methanimidamide acetate (1:1) are melted together for 1 hour at 140° C. Water is added to the melt. The solid product is filtered off and crystallized from 1-butanol, yielding 4.5 parts (68%) of 2,4-dihydro-4-[4-(4-methoxyphenyl)-1-piperazinyl]-3H-1,2,4-triazol-3-one.

EXAMPLE X

A mixture of 13 parts of N-[4-(4-methoxyphenyl)-1-piperazinyl]hydrazinecarboxamide, 14.2 parts of ethanimidamide hydrochloride, 12.3 parts of sodium acetate and 95 parts of 1,1'-oxybis[2-methoxyethane] is stirred for 3 hours at 130° C. The reaction mixture is poured onto water and the product is extracted twice with dichloromethane. The combined extracts are dried, filtered and evaporated. The residue is purified by column-chromatography over silica gel using a mixture of trichloromethane and methanol (98:2 by volume) as eluent. The pure fractions are collected and the eluent is evaporated. The residue is crystallized from 4-methyl-2-pentanone, yielding 5.1 parts (35%) of 2,4-dihydro-4-[4-(4-methoxyphenyl)-1-piperazinyl]-5-methyl-3H-1,2,4-triazol-3-one; mp. 264.3° C.

EXAMPLE XI

A mixture of 4.5 parts of 2,4-dihydro-4-[4-(4-methoxyphenyl)-1-piperazinyl]-3H-1,2,4-triazol-3-one, 0.8 parts of sodium hydride dispersion 78% and 27 parts of N,N-dimethylformamide is stirred for one hour at room temperature. Then there are added 2.5 parts of dimethyl sulfate and stirring at room temperature is continued for another hour. Water is added to the reaction mixture and the product is extracted twice with dichloromethane. The extract is dried, filtered and evaporated. The residue is purified by column-chromatography over silica gel using a mixture of trichloromethane and methanol (98:2 by volume) as eluent. The pure fractions are collected and the eluent is evaporated, yielding 3.3 parts (71%) of 2,4-dihydro-4-[4-(4-methoxyphenyl)-1-piperazinyl]-2-methyl-3H-1,2,4-triazol-3-one; mp. 178.2° C.

In a similar manner there is also prepared:
2,4-dihydro-4-[4-(4-methoxyphenyl)-1-piperazinyl]-2,5-dimethyl-3H-1,2,4-triazol-3-one; mp. 179.2° C.

EXAMPLE XII

A mixture of 3.1 parts of 1-(1H-imidazol-1-yl)-4-(4-methoxyphenyl)piperazine and 150 parts of a hydrobromic acid solution 48% in glacial acetic acid is stirred and refluxed overnight. The reaction mixture is evaporated and the residue is dissolved in water. Upon the addition of an excess of sodium hydrogen carbonate, the product is crystallized. It is filtered off and crystallized again from a mixture of N,N-dimethylformamide and water, yielding 2.8 parts (95%) of 4-[4-(1H-imidazol-1-yl)-1-piperazinyl]phenol; mp. 282.4° C.

There are also prepared following the same procedure and using equivalent amounts of the appropriate starting materials:
4-{4-[2-(methylthio)-1H-imidazol-1-yl]-1-piperazinyl}phenol; mp. 237° C.;
4-{4-[2-(ethylthio)-1H-imidazol-1-yl]-1-piperazinyl}phenol; mp. 178.2° C.;
4-[4-(2-pyridinyl)-1-piperazinyl]phenol; mp. 165.5° C.;
2,4-dihydro-4-[4-(4-hydroxyphenyl)-1-piperazinyl]-2-methyl-3H-1,2,4-triazol-3-one; mp. 210.3° C.; and
2,4-dihydro-4-[4-(4-hydroxyphenyl)-1-piperazinyl]-2,5-dimethyl-3H-1,2,4-triazol-3-one; mp. 262° C.

EXAMPLE XIII

A mixture of 2.9 parts of 4-[4-(2-pyridinyl)-1-piperazinyl]phenol, 0.4 parts of a sodium hydride dispersion 78% and 100 parts of dimethyl sulfoxide is stirred for 1 hour at 50° C. Then there are added 4.2 parts of cis-2-(2,4-dichlorophenyl)-2-(1H-imidazol-1-ylmethyl)-1,3-dioxolan-4-ylmethyl methanesulfonate and the whole is stirred for 3 hours at 100° C. The reaction mixture is cooled, water is added and the product is extracted three times with benzene. The combined extracts are dried, filtered and evaporated. The residue is crystallized from 1,1'-oxybisbutane (activated charcoal). The product is filtered off and dried, yielding 3.9 parts (68%) of cis-1-{4-[2-(2,4-dichlorophenyl)-2-(1H-imidazol-1-ylmethyl)-1,3-dioxolan-4-ylmethoxy]phenyl}-4-(2-pyridinyl)piperazine; mp. 155.6° C.

There are also prepared following the same procedure and using equivalent amounts of the appropriate starting materials:
cis-1-{4-[2-(2,4-dichlorophenyl)-2-(1H-imidazol-1-ylmethyl)-1,3-dioxolan-4-ylmethoxy]phenyl}-4-(1H-imidazol-1-yl)piperazine; mp. 189.5°–190° C.;
cis-1-{4-[2-(2,4-dichlorophenyl)-2-(1H-imidazol-1-ylmethyl)-1,3-dioxolan-4-ylmethoxy]phenyl}-4-[2-(methylthio)-1H-imidazol-1-yl]piperazine; mp. 149.1° C.;
cis-1-}4-[2-(2,4-dichlorophenyl)-2-(1H-imidazol-1-ylmethyl)-1,3-dioxolan-4-ylmethoxy]phenyl}-4-[2-(ethylthio)-1H-imidazol-1-yl]piperazine; mp. 124° C.;
cis-1-{4-[2-(2,4-dichlorophenyl)-2-(1H-imidazol-1-ylmethyl)-1,3-dioxolan-4-ylmethoxy]phenyl}-4-(2-thiazolyl)piperazine; mp. 152.5° C.;
cis-2-[4-{4-[2-(2,4-dichlorophenyl)-2-(1H-imidazol-1-ylmethyl)-1,3-dioxolan-4-ylmethoxy]phenyl}-1-piperazinyl]quinoline; mp. 155.2° C.;
cis-4-[4-{4-[2-(2,4-dichlorophenyl)-2-(1H-imidazol-1-ylmethyl)-1,3-dioxolan-4-ylmethoxy]-phenyl}-1-piperazinyl]-2,4-dihydro-2-methyl-3H-1,2,4-triazol-3-one ethanedioate (1:1) monohydrate, mp. 162.6° C.; and
cis-4-[4-{4-[2-(2,4-dichlorophenyl)-2-(1H-imidazol-1-ylmethyl)-1,3-dioxolan-4-ylmethoxy]phenyl}-1-piperazinyl]-2,4-dihydro-2,5-dimethyl-3H-1,2,4-triazol-3-one ethanedioate (1:1) monohydrate; mp. 163.7° C.

EXAMPLE XIV

To a stirred mixture of 2.9 parts of 4-[4-(1H-imidazol-1-yl)-1-piperazinyl]phenol and 75 parts of dimethyl sulfoxide are added 0.6 parts of a sodium hydride dispersion 50%. After stirring for 1 hour at room temperature, there are added 4.1 parts of cis-[2-(2,4-dichlorophenyl)-2-(1H-1,2,4-triazol-1-ylmethyl)-1,3-dioxolan-4-ylmethyl]methanesulfonate and the whole is stirred and heated for 6 hours at 100° C. The reaction mixture is cooled and poured onto water. The product is extracted twice with dichloromethane. The combined extracts are washed with water, with a diluted sodium hydroxide solution and again with water, dried, filtered and evaporated. The residue is crystallized from 4-methyl-2-pentanone, yielding 3.8 parts of cis-1-{4-[2-(2,4-dichlorophenyl)-2-(1H-1,2,4-triazol-1-ylmethyl)-1,3-dioxolan-4-ylmethoxy]phenyl}-4-(1H-imidazol-1-yl)piperazine hemihydrate; mp. 171.5° C.

There are also prepared following the same procedure and using equivalent amounts of the appropriate starting materials:
cis-1-{4-[2-(2,4-dichlorophenyl)-2-(1H-1,2,4-triazol-1-ylmethyl)-1,3-dioxolan-4-ylmethoxy]phenyl}-4-[2-(methylthio)-1H-imidazol-1-yl]piperazine; mp. 152.2° C.;
cis-1-{4-[2-(2,4-dichlorophenyl)-2-(1H-1,2,4-triazol-1-ylmethyl)-1,3-dioxolan-4-ylmethoxy]phenyl}-4-[2-(ethylthio)-1H-imidazol-1-yl]piperazine; mp. 114.8° C. and
cis-1-{4-[2-(2,4-dichlorophenyl)-2-(1H-1,2,4-triazol-1-ylmethyl)-1,3-dioxolan-4-ylmethoxy]phenyl}-4-(2-thiazolyl)piperazine; mp. 171.9° C.

EXAMPLE XV

A mixture of 1.9 parts of 2-chloro-3-nitropyridine, 4.9 parts of cis-1-{4-[2-(2,4-dichlorophenyl)-2-(1H-imidazol-1-ylmethyl)-1,3-dioxolan-4-ylmethoxy]phenyl}piperazine, 2 parts of potassium carbonate and 80 parts of 1-butanol is stirred and refluxed overnight. The reaction mixture is diluted with water and 90 parts of methylbenzene are added. The organic phase is separated, dried, filtered and evaporated. The residue is crystallized from 4-methyl-2-pentanone. The product is filtered off and dried, yielding 5.4 parts (88%) of cis-1-{4-[2-(2,4-dichlorophenyl)-2-(1H-imidazol-1-ylmethyl)-1,3-dioxolan-4-ylmethoxy]phenyl}-4-(3-nitro-2-pyridinyl)piperazine; mp. 145.5° C.

There are also prepared following the same procedure and using equivalent amounts of the appropriate starting materials:

cis-2-[4-{4-[2-(2,4-dichlorophenyl)-2-(1H-imidazol-1-ylmethyl)-1,3-dioxolan-4-ylmethoxy]phenyl}-1-piperazinyl]pyridine, N-oxide; mp. 186.7° C.;

cis-2-[4-{4-[2-(2,4-dichlorophenyl)-2-(1H-imidazol-1-ylmethyl)-1,3-dioxolan-4-ylmethoxy]phenyl}-1-piperazinyl]benzothiazole; mp. 157.7° C.;

cis-2-[4-{4-[2-(2,4-dichlorophenyl)-2-(1H-imidazol-1-ylmethyl)-1,3-dioxolan-4-ylmethoxy]phenyl}-1-piperazinyl]pyrimidine; mp. 178.5° C.;

cis-2-[4-{4-[2-(2,4-dichlorophenyl)-2-(1H-imidazol-1-ylmethyl)-1,3-dioxolan-4-ylmethoxy]phenyl}-1-piperazinyl]pyrazine; mp. 171.1° C. and cis-1-{4-[2-(2,4-dichlorophenyl)-2-(1H-1,2,4-triazol-1-ylmethyl)-1,3-dioxolan-4-ylmethoxy]phenyl}-4-(5-nitro-2-pyridinyl)piperazine; mp. 144.8° C.

EXAMPLE XVI

A mixture of 2.9 parts of 8-chloro-7-ethyl-3,7-dihydro-1,3-dimethyl-1H-purine-2,6-dione, 4.9 parts of cis-1-{4-[2-(2,4-dichlorophenyl)-2-(1H-imidazol-1-ylmethyl)-1,3-dioxolan-4-ylmethoxy]-phenyl}piperazine, 3 parts of potassium carbonate and 50 parts of dimethyl sulfoxide is stirred overnight at 130° C. The reaction mixture is diluted with water and the product is extracted twice with dichloromethane. The combined extracts are washed twice with water, dried, filtered and evaporated. The residue is purified by column-chromatography over silica gel using a mixture of trichloromethane and methanol (98:2 by volume) as eluent. The pure fractions are collected and the eluent is evaporated. The residue is crystallized from 4-methyl-2-pentanone. The product is filtered off and dried in vacuo at 150° C., yielding 5.6 parts (80%) of cis-8-[4-{4-[2-(2,4-dichlorophenyl)-2-(1H-imidazol-1-ylmethyl)-1,3-dioxolan-4-ylmethoxy]phenyl}-1-piperazinyl]-7-ethyl-3,7-dihydro-1,3-dimethyl-1H-purine-2,6-dione; mp. 205.4° C.

There are also prepared following the same procedure and using equivalent amounts of the appropriate starting materials:

cis-6-[4-{4-[2-(2,4-dichlorophenyl)-2-(1H-imidazol-1-ylmethyl)-1,3-dioxolan-4-ylmethoxy]phenyl}-1-piperazinyl]-3-pyridinecarboxamide; mp. 215.1° C.;

cis-1-{4-[2-(2,4-dichlorophenyl)-2-(1H-imidazol-1-ylmethyl)-1,3-dioxolan-4-ylmethoxy]phenyl}-4-(5-nitro-2-pyridinyl)piperazine; mp. 181.2° C.;

cis-2-[4-{4-[2-(2,4-dichlorophenyl)-2-(1H-imidazol-1-ylmethyl)-1,3-dioxolan-4-ylmethoxy]phenyl}-1-piperazinyl]-4-methylquinoline; mp. 153.1° C.;

cis-2-[4-{4-[2-(2,4-dichlorophenyl)-2-(1H-imidazol-1-ylmethyl)-1,3-dioxolan-4-ylmethoxy]phenyl}-1-piperazinyl]-3-methylquinoxaline; mp. 182.2°–187.2° C.;

cis-4-[4-{4-[2-(2,4-dichlorophenyl)-2-(1H-imidazol-1-ylmethyl)-1,3-dioxolan-4-ylmethoxy]phenyl}-1-piperazinyl]-2,6-dimethoxypyrimidine; mp. 131.1° C.;

cis-4-[4-{4-[2-(2,4-dichlorophenyl)-2-(1H-imidazol-1-ylmethyl)-1,3-dioxolan-4-ylmethoxy]phenyl}-1-piperazinyl]-2-(methylthio)pyrimidine monohydrate; mp. 103.1° C.;

cis-6-[4-[2-(2,4-dichlorophenyl)-2-(1H-imidazol-1-ylmethyl)-1,3-dioxolan-4-ylmethoxy]phenyl}-1-piperazinyl]-1,3,5-triazine-2,4-diamine ethanedioate (1:2); mp. 228.2° C.;

cis-2-[4-{4-[2-(2,4-dichlorophenyl)-2-(1H-imidazol-1-ylmethyl)-1,3-dioxolan-4-ylmethoxy]phenyl}-1-piperazinyl]-1-methyl-1H-benzimidazole; mp. 149.7° C.;

cis-2-[4-{4-[2-(2,4-dichlorophenyl)-2-(1H-imidazol-1-ylmethyl)-1,3-dioxolan-4-ylmethoxy]phenyl}-1-piperazinyl]-1-ethyl-1H-benzimidazole ethanedioate (1:2) monohydrate; mp. 158.1° C. and cis-8-[4-{4-[2-(2,4-dichlorophenyl)-2-(1H-imidazol-1-ylmethyl)-1,3-dioxolan-4-ylmethoxy]phenyl}-1-piperazinyl]-3,7-dihydro-1,3,7-trimethyl-1H-purine-2,6-dione; mp. 198.6° C.

EXAMPLE XVII

A mixture of 1.3 parts of 2-bromo-5-nitrothiazole, 3 parts of cis-1-{4-[2-(2,4-dichlorophenyl)-2-(1H-imidazol-1-ylmethyl)-1,3-dioxolan-4-ylmethoxy]phenyl}piperazine, 2 parts of potassium carbonate and 90 parts of N,N-dimethylformamide is stirred for 3 hours at 60° C. The reaction mixture is diluted with water and the product is extracted with trichloromethane. The extract is dried, filtered and evaporated. The residue is crystallized from 1-butanol. The product is filtered off and dried, yielding 2.4 parts (63%) of cis-2-[4-{4-[2-(2,4-dichlorophenyl)-2-(1H-imidazol-1-ylmethyl)-1,3-dioxolan-4-ylmethoxy]phenyl}-1-piperazinyl]-5-nitrothiazole; mp. 219.2° C.

EXAMPLE XVIII

A mixture of 3.2 parts of 2-chloro-6-ethoxypyridine, 4.9 parts of cis-1-{4-[2-(2,4-dichlorophenyl)-2-(1H-imidazol-1-ylmethyl)-1,3-dioxolan-4-ylmethoxy]phenyl}piperazine and 2 parts of potassium carbonate is stirred and heated for 48 hours at 140° C. The reaction mixture is cooled and purified twice by column-chromatography over silica gel using first trichloromethane and then a mixture of methylbenzene and ethanol (95:5 by volume) as eluent. The pure fractions are collected at the eluent is evaporated. The residue is triturated in 2,2'-oxybispropane. The product is filtered off and dried, yielding 1.2 parts (20%) of cis-1-{4-[2-(2,4-dichlorophenyl)-2-(1H-imidazol-1-ylmethyl)-1,3-dioxolan-4-ylmethoxy]phenyl}-4-(6-ethoxy-2-pyridinyl)piperazine; mp. 132.7° C.

EXAMPLE XIX

Following the procedure described in Example IX and using equivalent amounts of the appropriate starting materials there are also prepared:

1-{3-[2-(2,4-dimethoxyphenyl)-2-(1H-1,2,4-triazol-1-ylmethyl)-1,3-dioxolan-4-ylmethoxy]phenyl}-4-{4-methyl-5-(phenylmethyl)-1H-imidazol-1-yl]piperazine;

trans 1-{4-[2-(5-chloro-2-thienyl)-2-(1H-1,2,4-triazol-1-ylmethyl)-1,3-dioxolan-4-ylmethoxy]phenyl}-4-[2-(4-fluorophenylthio)-5-phenyl-1H-imidazol-1-yl]piperazine;

cis-1-{3-[2-(4-methylphenyl)-2-(1H-1,2,4-triazol-1-ylmethyl)-1,3-dioxolan-4-ylmethoxy]phenyl}-4-(4-nitro-5-phenylmethyl-2-thiazolyl)piperazine and 1-{4-[2-(2-thienyl)-2-(1H-1,2,4-triazol-1-ylmethyl)-1,3-dioxolan-4-ylmethoxy]phenyl}-4-(5-phenyl-2-thiazolyl)piperazine.

EXAMPLE XX

Following the procedure described in Example X and using equivalent amounts of the appropriate starting materials there are also prepared:

1-{4-[2-(3-ethoxyphenyl)-2-(1H-imidazol-1-ylmethyl)-1,3-dioxolan-4-ylmethoxy]phenyl}-4-(5-ethyl-4-phenyl-1H-imidazol-1-yl)piperazine;
trans-1-{3-[2-(4-bromo-2-thienyl)-2-(1H-imidazol-1-ylmethyl)-1,3-dioxolan-4-ylmethoxy]phenyl}-4-[2-(phenylmethylthio)-1H-imidazol-1-yl]piperazine;
cis-1-{4-[2-(4-ethoxyphenyl)-2-(1H-imidazol-1-ylmethyl)-1,3-dioxolan-4-ylmethoxy]phenyl}-4-(2-thiazolyl)piperazine and
1-{3-[2-(3-bromo-2-thienyl)-2-(1H-imidazol-1-ylmethyl)-1,3-dioxolan-4-ylmethoxy]phenyl}-4-[5-(4-methylpheny)-4-nitro-2-thiazolyl]piperazine.

EXAMPLE XXI

Following the procedure described in Example XII and using equivalent amounts of the appropriate starting materials there are also prepared:
cis-1-{4-[2-(4-ethylphenyl)-2-(1H-imidazol-1-ylmethyl)-1,3-dioxolan-4-ylmethoxy]phenyl}-4-(3-fluoro-4-methoxy-2-pyridinyl)piperazine;
5-[4-{4-[2-(4-chloro-2-thienyl)-2-(1H-1,2,4-triazol-1-ylmethyl)-1,3-dioxolan-4-ylmethoxy]phenyl}-1-piperazinyl]-2-pyridinamine;
trans-6-[4-{[ 3-[2-(3-ethoxyphenyl)-2-(1H-imidazol-1-ylmethyl)-1,3-dioxolan-4-ylmethoxy]phenyl}-1-piperazinyl]-2-pyridinol;
2-[4-{4-[2-(1H-imidazol-1-ylmethyl)-2-(2-thienyl)-1,3-dioxolan-4-ylmethoxy]phenyl}-1-piperazinyl]-pyridine, N-oxide;
cis-2-[4-{3-[2-(1H-imidazol-1-ylmethyl)-2-phenyl-1,3-dioxolan-4-ylmethoxy]phenyl}-1-piperazinyl]-5-pyrazinol;
2-[4-{4-[2-(4-bromophenyl)-2-(1H-1,2,4-triazol-1-ylmethyl)-1,3-dioxolan-4-ylmethoxy]phenyl}-1-piperazinyl]-3-nitropyrazine;
trans-3-chloro-2-[4-{3-[2-(1H-imidazol-1-ylmethyl)-2-(2,4,6-trimethylphenyl)-1,3-dioxolan-4-ylmethoxy]phenyl}-1-piperazinyl]-5-methoxypyrazine;
2-[4-{4-[2-(3-chloro-2-thienyl)-2-(1H-1,2,4-triazol-1-ylmethyl)-1,3-dioxolan-4-ylmethoxy]phenyl}-1-piperazinyl]pyrazine;
cis-2-[4-{3-[2-(1H-imidazol-1-ylmethyl)-2-(2-thienyl)-1,3-dioxolan-4-ylmethoxy]phenyl}-1-piperazinyl]-6-methylpyrazine;
cis-2-[4-{3-[2-(4-fluorophenyl)-2-(1H-imidazol-1-ylmethyl)-1,3-dioxolan-4-ylmethoxy]phenyl}-1-piperazinyl]-3-methoxyquinoline;
cis-3-nitro-2-[4-{4-[2-(2-thienyl)-2-(1H-1,2,4-triazol-1-ylmethyl)-1,3-dioxolan-4-ylmethoxy]phenyl}-1-piperazinyl]quinoline;
trans-2-[4-{4-[2-(5-chloro-2-thienyl)-2-(1H-1,2,4-triazol-1-ylmethyl)-1,3-dioxolan-4-ylmethoxy]phenyl}-1-pierazinyl]-3-methoxyquinoxaline;
2-[4-{2-[2-(1H-imidazol-1-ylmethyl)-2-(4-trifluoromethylphenyl)-1,3-dioxolan-4-ylmethoxy]phenyl}-1-piperazinyl]-3-chloroquinoxaline;
cis-2-[4-{3-[2-(1H-imidazol-1-ylmethyl)-2-(3-methoxyphenyl)-1,3-dioxolan-4-ylmethoxy]phenyl}-1-piperazinyl]-3-nitropyrimidine;
cis-2-[4-{4-[2-(2-thienyl)-2-(1H-1,2,4-triazol-1-ylmethyl)-1,3-dioxolan-4-ylmethoxy]phenyl}-1-piperazinyl]pyrimidine;
trans-2-[4-{4-[2-(1H-imidazol-1-ylmethyl)-2-(4-pentylphenyl)-1,3-dioxolan-4-ylmethoxy]phenyl}-1-piperazinyl]-1,3,5-triazine;
2-[4-{3-[2-(4-bromo-2-thienyl)-2-(1H-1,2,4-triazol-1-ylmethyl)-1,3-dioxolan-4-ylmethoxy]phenyl}-1-piperazinyl]-6-nitro-1,3,5-triazine;
cis-4-[4-{4-[2-(4-bromo-2-thienyl)-2-(1H-imidazol-1-ylmethyl)-1,3-dioxolan-4-ylmethoxy]phenyl}-1-piperazinyl]-5-methyl-2-(phenylmethylthio)pyrimidine;
4-[4-{3-[2-(4-bromophenyl)-2-(1H-1,2,4-triazol-1-ylmethyl)-1,3-dioxolan-4-ylmethoxy]phenyl}-1-piperazinyl]-6-ethoxy-2-pyrimidinamine;
2-[4-{4-[2-(3-ethoxyphenyl)-2-(1H-imidazol-1-ylmethyl)-1,3-dioxolan-4-ylmethoxy]phenyl}-1-piperazinyl]-1-(phenylmethyl)-1H-benzimidazole;
trans-2-[4-{4-[2-(5-bromo-2-thienyl)-2-(1H-1,2,4-triazol-1-ylmethyl-1,3-dioxolan-4-ylmethoxy]phenyl}-1-piperazinyl]-1-propyl-1H-benzimidazole;
8-[4-{4-[2-(1H-imidazol-1-ylmethyl)-2-(2,4,6-trichlorophenyl)-1,3-dioxolan-4-ylmethoxy]phenyl}-1-piperazinyl]-7-ethyl-3,7-dihydro-1,3-dipropyl-1H-purine-2,6-dione and
cis-8-[4-{3-[2-(2-thienyl)-2-(1H-1,2,4-triazol-1-ylmethyl)-1,3-dioxolan-4-ylmethoxy]phenyl}-1-piperazinyl]-3,7-dihydro-1,3-dimethyl-7-(phenylmethyl)-1H-purine-2,6-dione.

What is claimed is:
1. A chemical compound selected from the group consisting of an azole derivative having the formula:

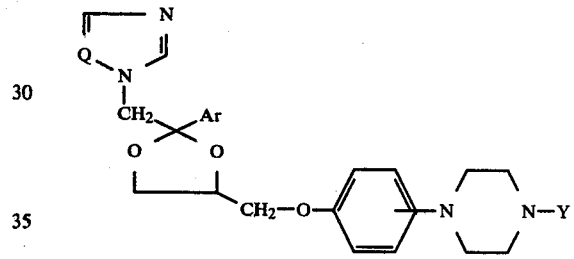

and the pharmaceutically acceptable acid addition salts and stereochemically isomeric forms thereof, wherein:
Q is a member selected from the group consisting of CH and N;
Ar is a member selected from the group consisting of phenyl, thienyl, halothienyl and substituted phenyl, said substituted phenyl having from 1 to 3 substituents each independently selected from the group consisting of halo, lower alkyl, lower alkyloxy and trifluoromethyl; and
the radical Y is an optionally substituted mono- or binuclear nitrogen-containing heteroaromatic radical selected from the group consisting of:
a radical of formula

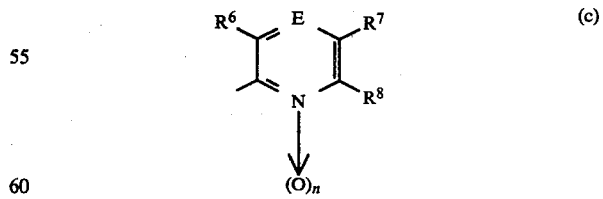

(c)

wherein n is the integer 0 or 1, E is a member selected from the group consisting of N and C—$R^9$ and $R^6$, $R^7$, $R^8$ and $R^9$ are each independently selected from the group consisting of hydrogen, halo, lower alkyl, lower alkyloxy, lower alkylthio, hydroxy, mercapto, nitro, amine and aminocarbonyl, or, $R^7$ and $R^8$, when taken together, represent a radical of the formula
—CH=CH—CH=CH—;
a radical of formula

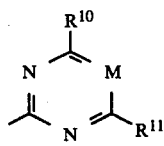 (d)

wherein M is a member selected from the group consisting of N and C—$R^{12}$ and $R^{10}$,$R^{11}$ and said $R^{12}$ are each independently selected from the group consisting of hydrogen, halo, lower alkyl, nitro and amino; and
a radical of formula

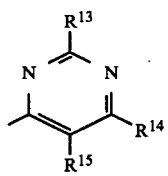 (e)

wherein $R^{14}$ and $R^{15}$ are each independently selected from the group consisting of hydrogen, halo, lower alkyl, lower alkyloxy, aryl and aryl-lower alkyl and $R^{13}$ is selected from the group consisting of hydrogen, halo, amino, lower alkylthio, aryllower alkylthio and lower alkyloxy.

2. A composition for combatting the growth of a microorganism selected from the group consisting of fungus and bacterium comprising an inert carrier material and as an active ingredient an effective antifungal or antibacterial amount of a compound selected from the group consisting of an azole derivative having the formula:

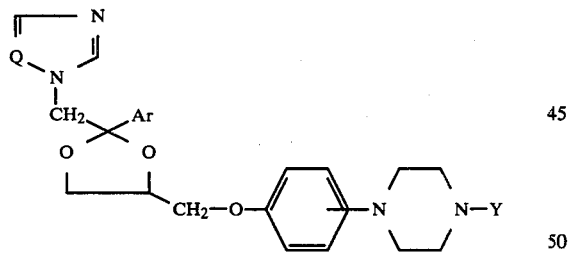

and the pharmaceutically acceptable acid addition salts and stereochemically isomeric forms thereof, wherein:
Q is a member selected from the group consisting of CH and N;
Ar is a member selected from the group consisting of phenyl, thienyl, halothienyl and substituted phenyl, said substituted phenyl having from 1 to 3 substituents each independently selected from the group consisting of halo, lower alkyl, lower alkyloxy and trifluoromethyl; and
the radical Y is an optionally substituted mono- or binuclear nitrogen-containing heteroaromatic radical selected from the group consisting of:
a radical of formula

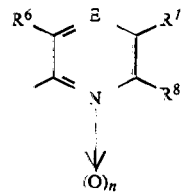 (c)

wherein n is the integer 0 or 1, E is a member selected from the group consisting of N and C—$R^9$ and $R^6$, $R^7$, $R^8$ and $R^9$ are each independently selected from the group consisting of hydrogen, halo, lower alkyl, lower alkyloxy, lower alkylthio, hydroxy, mercapto, nitro, amino and aminocarbonyl, or, $R^7$ and $R^8$, when taken together, represent a radical of the formula
—CH=CH—CH=CH—;
a radical of formula

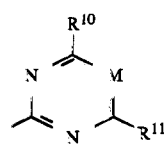 (d)

wherein M is a member selected from the group consisting of N and C—$R^{12}$ and $R^{10}$, $R^{11}$ and said $R^{12}$ are each independently selected from the group consisting of hydrogen, halo, lower alkyl, nitro and amino; and
a radical of formula

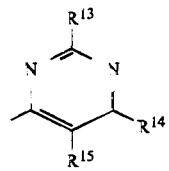 (e)

wherein $R^{14}$ and $R^{15}$ are each independently selected from the group consisting of hydrogen, halo, lower alkyl, lower alkyloxy, aryl and aryl-lower alkyl and $R^{13}$ is selected from the group consisting of hydrogen, halo, amino, lower alkylthio, aryllower alkylthio and lower alkyloxy.

* * * * *